United States Patent [19]

Davies

[11] Patent Number: 5,439,894
[45] Date of Patent: Aug. 8, 1995

[54] DEXTRIN DERIVATIVES FOR THE TREATMENT OF ACIDIC CONDITIONS

[75] Inventor: Donald S. Davies, Buckinghamshire, Great Britain

[73] Assignee: M L Laboratories PLC, London, United Kingdom

[21] Appl. No.: 150,717

[22] Filed: Nov. 12, 1993

Related U.S. Application Data

[62] Division of Ser. No. 640,313, Jan. 29, 1991, Pat. No. 5,280,017.

[51] Int. Cl.6 .................... A61K 31/73; A61K 31/715
[52] U.S. Cl. ........................ 514/58; 514/819; 514/823; 536/46; 536/103
[58] Field of Search .................. 514/58, 819, 823; 536/46, 103

[56] References Cited

U.S. PATENT DOCUMENTS

| | | | |
|---|---|---|---|
| 2,813,093 | 11/1957 | Caldwell et al. | 536/102 |
| 3,639,389 | 2/1972 | Hull | 536/102 |
| 4,129,722 | 12/1978 | Iovine et al. | 536/43 |
| 4,179,382 | 12/1979 | Rudkin et al. | 252/8.8 |
| 4,344,968 | 8/1982 | Aoda et al. | 424/DIG. 14 |
| 5,059,685 | 10/1991 | Conti | 536/1.11 |
| 5,169,562 | 12/1992 | Mitchell et al. | 536/46 |
| 5,258,175 | 11/1993 | Davies | 536/46 |
| 5,280,017 | 1/1994 | Davies | 514/58 |

FOREIGN PATENT DOCUMENTS

| | | |
|---|---|---|
| 0066135A1 | 5/1982 | European Pat. Off. . |
| 0212145A1 | 6/1986 | European Pat. Off. . |
| 2353633 | 6/1977 | France . |
| 2154469A | 9/1985 | United Kingdom . |

OTHER PUBLICATIONS

Kerr et al., (1952), *Die Starke*, [4]10:253,256,257.

*Primary Examiner*—Ronald W. Griffin
*Attorney, Agent, or Firm*—Darby & Darby

[57] ABSTRACT

Disclosed is a pharmaceutical composition comprising a dextrin derivative in which a proportion of the hydroxyl groups of dextrin are replaced by basic groups. Such compositions are useful for the treatment of acidic conditions.

10 Claims, 1 Drawing Sheet

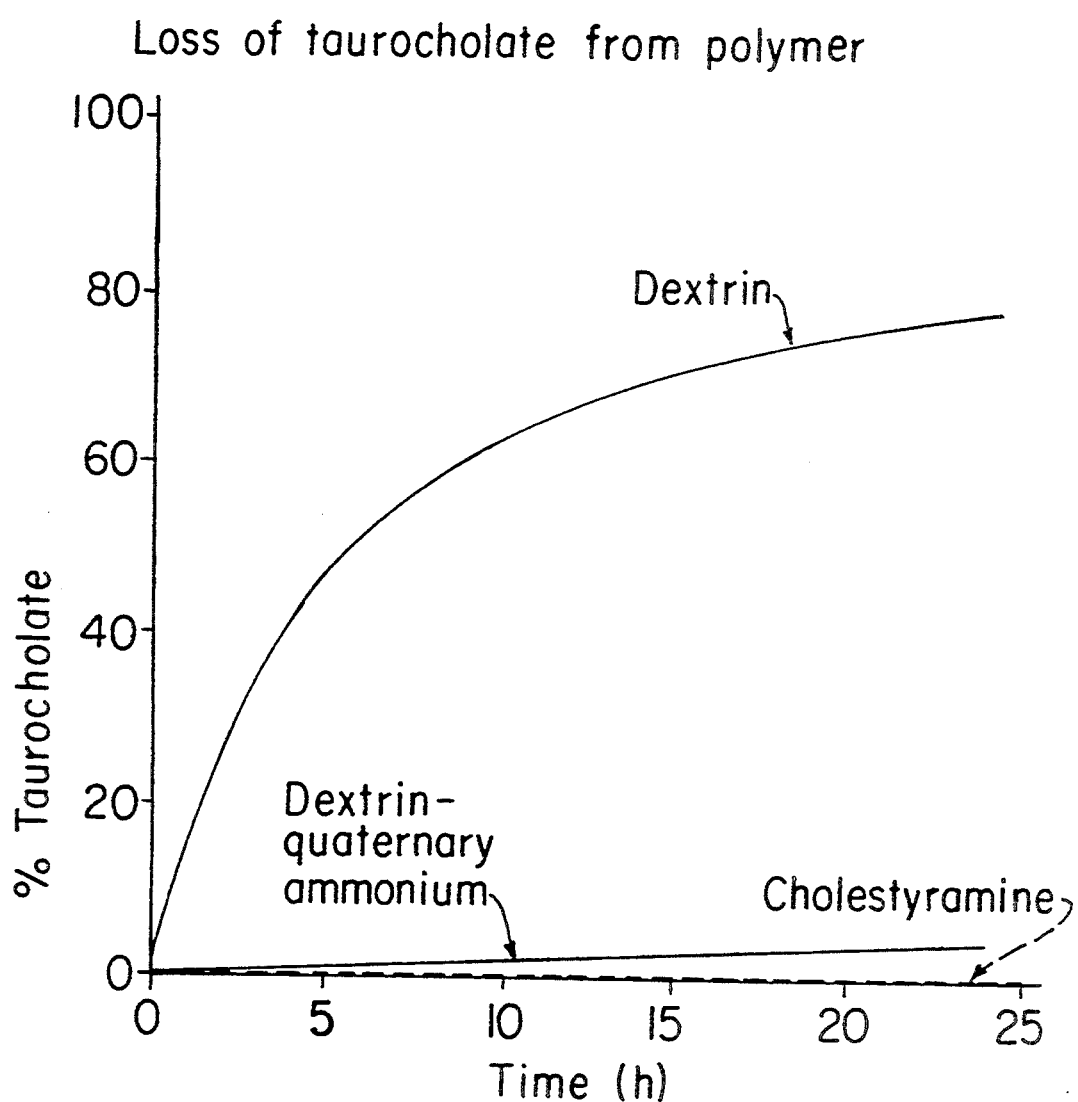

DEXTRIN DERIVATIVES FOR THE TREATMENT OF ACIDIC CONDITIONS

This is a division of application Ser. No. 07/640,313, filed Jan. 29, 1991, now U.S. Pat. No. 5,280,017.

This invention relates to certain dextrin derivatives, the treatment of acidic conditions and to compositions for the use in such treatment.

According to a first aspect of the present invention, there is provided a dextrin derivative in which a proportion of the hydroxyl groups of dextrin are replaced by basic groups. Such basic groups may be any groups capable of binding acidic moieties present in body compartments such as the intestine, the peritoneum or the blood compartment. A preferred basic group is an amine group, more preferably a tertiary amine or a quaternary ammonium group.

It is well known that the binding of bile acids, which are secreted into the intestines, leads to a feedback activation of enzymes in the liver which metabolise cholesterol. This results in a lowering of blood cholesterol levels. Two agents are known for regulating the level of cholesterol by binding with the bile acids. Cholestyramine is the chloride salt of a basic anion-exchange resin in which the anion-exchange sites are provided by quaternary ammonium groups. The other agent is a resin called colestipol hydrochloride, a copolymer of diethyl pentamine and epichlorohydrin. Both these materials are hydrophilic but insoluble in water. They are unaffected by digestive enzymes, they remain unchanged in the gastro-intestinal tract and they are not absorbed into the bloodstream. However, these agents are resins and as a result have a sandy or gritty quality which makes them unpleasant to assimilate. In addition, they may cause nausea, abdominal discomfort, indigestion and constipation. Furthermore, in the case of cholestyramine, which is a chloride form of an anion-exchange resin, hyperchloremic acidosis can occur, especially in younger and smaller patients in whom the relative dosage is higher.

Another problem with these known agents is that they may also bind other compounds in the intestine including drugs administered concurrently.

Acid poisoning can occur as a result not only of the assimilation of substances which are normally regarded as poisons but also of pharmaceutical preparations which can be poisonous if taken in overdose. Examples of acid poisons include acetylsalicylic acid (aspirin) and barbiturates such as amylobarbitone, butobarbitone, pentobarbitone, phenobarbitone and quinalbarbitone.

The present invention accordingly also provides the use of the dextrin derivative to lower blood cholesterol levels and to treat acid poisoning. The present invention further provides a pharmaceutical composition comprising the dextrin derivative of the invention together with a inert carrier or diluent therefor. In addition the present invention provides a method for lowering blood cholesterol levels or treating acid poisoning in an animal subject, including a human being, comprising administering to the animal subject an effective amount of a dextrin derivative of the invention.

In a further aspect the invention provides a method of making a pharmaceutical composition of the invention comprising formulating together a dextrin derivative of the invention together with at least one inert carrier or diluent.

Dextrin is made by hydrolysis of starch, typically by treatment of various starches with dilute acids or by heating a dry starch. Such methods produce glucose polymers with a large range of polymerisation. The degree of polymerisation (D.P) varies from one or two up to comparatively high numbers. The direct hydrolysis product of starch might contain up to 60% by weight of material having a D.P. less than 12. In a preferred aspect of the present invention the dextrin derivative contains a relatively high proportion of glucose polymers of D.P. greater than 12. Preferably the dextrin derivative contains at least 50% by weight of glucose polymers of D.P. greater than 12.

More preferably the dextrin derivative contains less than 10% by weight of glucose polymers having a D.P. less than 12. Most preferably the dextrin derivative contains less than 5% by weight of glucose polymers having a D.P. less than 12. Such dextrin derivatives are prepared from dextrin which has been fractionated to remove dextrin with a low D.P. Known fractionation techniques may be used including solvent precipitation and membrane fractionation.

A method of preparing a glucose polymer mixture is described in GB 2132914 and a method for the preparation of a glucose polymer mixture with a relatively low proportion of low D.P. glucose polymers is described in Example 2 of GB 2154469. This mixture contains 91.9% of polymers having a degree of polymerisation greater than 12 and 7.9% of polymers having a degree of polymerisation from 2 to 10.

The weight average molecular weight of the dextrin derivative of use in the present invention is preferably from 15,000 to 25,000, more preferably from 15,000 to 20,000. The number average molecular weight is preferably less than 5,000. The weight average molecular weight is determined by high pressure liquid chromatography (HPLC). The method is carried out on dextrin (rather than the dextrin derivative) using chromatographic columns calibrated with dextran standards, as described by Alsop et al, J. Chromatography 246, 227–240 (1982).

It is preferred that, particularly in the case of the lowering of blood cholesterol levels, the very high molecular weight glucose polymers are not present or are only present in small amounts in the dextrin derivative mixture.

The composition in accordance with the present invention may be made up for administration by any suitable route. By way of examples, the composition may be for oral administration or, in the case of treatment of acid poisoning, for administration via the peritoneum.

Basic derivatives of dextrin represent new chemical compounds. They can be prepared in various ways. For instance, they may be prepared by methods analogous to those described for the preparation of ethers having a tertiary amine group as described in U.S. Pat. Nos. 2,813,093, 2,917,506, 2,935,436 and 2,975,124, or, for the preparation of quaternary ammonium compounds, as described in U.S. Pat. No. 2,876,217.

The properties of basic derivatives of dextrin depend on the nature and content of the basic groups. It is preferred that the derivative is water soluble. The content of the basic group is preferably at least 5% by weight, the upper limit being determined in practice by the difficulty of introducing much more than 10% by weight of the basic group into the dextrin, using currently available techniques.

For oral administration, compositions containing derivatives of dextrin can be used. These compositions have the advantage that they are water soluble and their taste or colour can be disguised by adding, for instance, synthetic food additives. By drinking a mixture containing the dextrin derivative the active material immediately reaches the intestine where it acts to bind bile acids or acid poisions. The rapid delivery of the active ingredient to its target, the bile acids or the the acid poisons, has the advantage that no degeneration occurs before the active ingredient reaches the site of the target.

A composition for peritoneal administration may also include electrolytes similar to those contained in conventional solutions used in peritoneal dialysis. For example, they may include electrolytes in the following concentration (all in mmol/l):

| | |
|---|---|
| Na | 115 to 140 |
| Cl | 95 to 145 |
| Mg | 0.6 to 0.9 |
| Ca | 1.0 to 5.0 |
| Lactate | 30 to 40. |

The nature and the contents of the electrolytes are, however, not so important as in conventional peritoneal dialysis, because the treatment of cholesterol levels or of acid poisoning is a short-term operation. Nevertheless, electrolyte imbalance can cause serious problems in poisoned patients, and the present of suitable electrolytes in the dialysis is recommended.

On the other hand, it is important that the compositions of the invention contain an osmotic agent in a concentration capable of producing efficient and sustained ultrafiltration (a term used to mean the net flow of fluid across the peritoneal membrane into the peritoneal cavity). The osmotic agent in the compositions of the invention is normally the dextrin derivative itself, although it can be supplemented, when appropriate, by the inclusion of other osmotic agents, for example dextrose or a mixture of glucose polymers.

BRIEF DESCRIPTION OF THE DRAWING

The drawing is a graph showing loss of taurocholate with time from dextrin, dextrin-quaternary ammonium, and cholestyramine.

An example of the present invention will now be described.

A quaternary ammonium alkyl dextrin (specifically quaternary ammonium hydroxyethyl dextrin) was prepared in the following manner. Triethylamine (45 g) was suspended in water (100 ml) and stirred at room temperature. Then epichlorohydrin (37 g, 0.4 mole) was added dropwise. Stirring was continued for 5 hours but the mixture was still not homogeneous. After stirring overnight the resultant homogeneous solution was evaporated at 30° C. in vacuo to a thick syrup over several hours. Dextrin (20 g—as prepared in Example 2 of GB2154469 and which contains 91.9% of DP>12 and 7.9% of DP 2 to 10) in water (60 ml) was added to give a viscous solution and then NaOH (2.8 g) in water (15 ml) was added. This gave a thick gummy precipitate and more water (100 ml) was added with stirring until a solution was obtained. This was stirred overnight at room temperature, and the reaction mixture was neutralised with 4M HCl. It was dialysed for 3 days against tap water and for 2 days against distilled water. The final solution was freeze dried to give 29.8 g of a glassy powder. The NMR (nuclear magnetic resonance) spectrum indicates about 1 quaternary ammonium group per glucose in the substitute dextrin.

The ability of the quarternary ammonium ethyl dextrin to bind bile acids was compared with unsubstituted dextrin and with cholestyramine. The relative affinities of these materials for taurocholic acid were determined. To 4 ml of 2.5% solutions of dextrin and the dextrin derivative and to 2.5% suspension of cholestyramine in distilled water was added 1 ml of an aqueous solution containing 10 mg of $^{14}$C-taurocholate ($5.5 \times 10^5$ dpm). After 15 minutes the 5 ml solutions were placed in dialysis bags and dialyzed against 100 ml of water. Timed samples were taken from the dialysis bag (0.1 ml) and the dialysate (5 ml) and radioactivity was counted in a Liquid Scintillation Spectrometer.

The results are shown in the accompanying drawing which is a graph showing loss of taurocholate with time for the three materials. It can be seen the substituted dextrin and cholestyramine both strongly bind taurocholic acid, less than 5% being lost from the dialysis bag in 24 hours. By comparison, dextrin does not bind the bile acid, 80% being lost in 24 hours.

The substituted dextrin can accordingly be used to lower blood cholesterol levels but without the above mentioned disadvantages associated with the use of cholestyramine.

Studies conducted in vitro have demonstrated that the above-prepared dextrin derivative avidly binds acidic drugs such as salicylic acid or phenobarbitone in the manner described above for taurocholic acid. To further demonstrate the utility of the dextrin derivative in binding acidic molecules in body compartments a study has been conducted in rats.

Rats were dosed intravenously with radio-labelled phenobarbitone and after 15 minutes 10 ml of a 2% solution of the dextrin derivative was introduced into the peritoneum. For comparison a 2% solution of unsubstituted dextrin was used as a control. The experiment was conducted on two occasions with 3 animals in each treatment group. One hour after the introduction of the solutions into the peritoneal cavity, simultaneous samples of blood and peritoneal fluid were obtained and analysed for radio-labelled phenobarbitone. Peritoneal fluid/blood plasma ratios for phenobarbitone at 3 hours are given below.

| | Dialysate fluid/blood plasma ratio | |
|---|---|---|
| Dialysate | Experiment 1 | Experiment 2 |
| 2% Dextrin | 0.89 | 0.94 |
| 2% Dextrin derivative | 2.32 | 2.68 |

The results show that phenobarbitone accumulates in the peritoneal cavity fluid against a concentration gradient when the basic dextrin derivative is present but not with dextrin. This is despite the fact that the rat is a poor model for man because of rapid loss of polymer from the peritoneal cavity. This demonstrates that a basic dextrin derivative can be used to enhance clearance of acidic chemicals from the blood stream during the treatment of poisoning by peritoneal dialysis.

I claim:

1. A pharmaceutical composition comprising a dextrin derivative in which a proportion of the hydroxyl groups of dextrin are replaced by amine groups or residues, said amine groups or residues being present in an amount of at least 0.5 group per glucose unit, and at least one pharmaceutically acceptable carrier or diluent.

2. The pharmaceutical composition of claim 1 wherein the amine groups or residues are tertiary amine or quaternary ammonium groups or residues.

3. The pharmaceutical composition of claim 2 wherein the tertiary amine or quaternary ammonium groups or residues are present in an amount of from 0.5 to 2 groups per glucose unit.

4. The pharmaceutical composition of claim 3 wherein the tertiary amine or quaternary ammonium groups or residues are present in an amount of from 0.5 to 1.5 per glucose unit.

5. The pharmaceutical composition of claim 1 wherein not more than 10% by weight of the dextrin derivative is in the form of glucose polymers having a degree of polymerization of less than 12.

6. The pharmaceutical composition of claim 3 wherein not more than 5% by weight of the dextrin derivative is in the form of glucose polymers having a degree of polymerization of less than 12.

7. The pharmaceutical composition of claim 1 wherein the weight average molecular weight of the dextrin derivative is from 15,000 to 25,000.

8. The pharmaceutical composition of claim 1, adapted for intraperitoneal administration.

9. The pharmaceutical composition of claim 1, adapted for oral administration.

10. A pharmaceutical composition comprising a dextrin derivative in which a proportion of the hydroxyl groups of dextrin are replaced by amine groups or residues, said amine groups or residues being present in an amount of from 0.5 to 1.5 groups per glucose unit, wherein not more than 5% by weight of the dextrin derivatives is in the form of a glucose polymer having a degree of polymerization of less than 12 and wherein the weight average molecular weight of the dextrin derivative is from 15,000 to 25,000, and said amine groups or residues are tertiary amine or quaternary ammonium groups or residues, and further comprising at least one pharmaceutically acceptable carrier or diluent.

* * * * *